United States Patent
Murthy et al.

(10) Patent No.: US 7,151,189 B2
(45) Date of Patent: Dec. 19, 2006

(54) METHOD AND APPARATUS FOR WASTE STREAM RECOVERY

(75) Inventors: Vutukuru Lakshmi Narasimha Murthy, Bangalore (IN); Ignacio Fernandez Vic, Las Matas (ES); Boddapaty Venkata Venugopal, Bangalore (IN)

(73) Assignee: General Electric Company, Schenectady, NY (US)

( * ) Notice: Subject to any disclaimer, the term of this patent is extended or adjusted under 35 U.S.C. 154(b) by 511 days.

(21) Appl. No.: 10/250,269

(22) Filed: Jun. 19, 2003

(65) Prior Publication Data
US 2005/0010063 A1     Jan. 13, 2005

(51) Int. Cl.
*C07C 69/88* (2006.01)
*C07C 69/96* (2006.01)

(52) U.S. Cl. .............. 558/270; 558/274; 526/270; 528/196

(58) Field of Classification Search ........... 558/270, 558/274; 526/270; 528/196
See application file for complete search history.

(56) References Cited

U.S. PATENT DOCUMENTS

| | | | |
|---|---|---|---|
| 4,012,406 A | 3/1977 | Buysch et al. | |
| 4,789,730 A | 12/1988 | Priddy | |
| 5,026,817 A | 6/1991 | Sakashita et al. | |
| 5,236,959 A | 8/1993 | Oakley et al. | |
| 5,266,716 A | 11/1993 | Buysch et al. | |
| 5,334,742 A | 8/1994 | Schon et al. | |
| 5,440,066 A | 8/1995 | Buysch et al. | |
| 5,602,271 A | 2/1997 | Ooms et al. | |
| 5,747,609 A | 5/1998 | Komiya et al. | |
| 5,980,445 A | 11/1999 | Mizukami et al. | |
| 6,175,017 B1 | 1/2001 | Buysch et al. | |
| 6,184,334 B1 | 2/2001 | McCloskey et al. | |
| 6,262,210 B1 | 7/2001 | Tojo et al. | |
| 6,294,684 B1 * | 9/2001 | de Bruin et al. | 558/274 |
| 6,323,304 B1 | 11/2001 | Lemmon et al. | |
| 6,339,138 B1 | 1/2002 | van Hout et al. | |
| 6,395,862 B1 | 5/2002 | Lemmon et al. | |
| 6,403,754 B1 | 6/2002 | McCloskey et al. | |
| 6,420,588 B1 * | 7/2002 | McCloskey et al. | 558/274 |
| 6,469,192 B1 * | 10/2002 | Burnell et al. | 558/274 |
| 6,479,689 B1 | 11/2002 | Tojo et al. | |
| 6,506,871 B1 | 1/2003 | Silvi et al. | |
| 2003/0050427 A1 | 3/2003 | Brunelle et al. | |

OTHER PUBLICATIONS

JP2002212335. Publication Date: Jul. 31, 2002. Abstract Only. (1 page).
International Search Report dated Dec. 29, 2004.

* cited by examiner

*Primary Examiner*—Johanna Richter
*Assistant Examiner*—Chukwuma Nwaonicha (57) ABSTRACT

A method for recovering a product mixture from a waste stream in a diaryl carbonate manufacturing process comprising reacting the waste stream with an alkyl alcohol to form a reaction mixture, and separating the product mixture from the reaction mixture.

43 Claims, 4 Drawing Sheets

METHOD AND APPARATUS FOR WASTE STREAM RECOVERY

BACKGROUND OF INVENTION

This disclosure relates to a method for recovering valuable compounds from a waste generated from a diaryl carbonate manufacturing process.

Diaryl carbonates, such as diphenyl carbonate are an important reactant in the production of polycarbonate resins. As the use of polycarbonate resins has increased, the efficient production of diaryl carbonate has become more important. The transesterification method for diaryl carbonate production involves two reaction steps. First, a dialkyl carbonate reacts with an aromatic alcohol to produce an alkyl aryl carbonate and an alkyl alcohol in presence of a transesterification catalyst. Next, two molecules of the alkyl aryl carbonate undergo a disproportionation reaction to produce one molecule of diaryl carbonate and one molecule of dialkyl carbonate. Diaryl carbonates can also be produced by reacting phenol with phosgene.

The waste streams from the diaryl carbonate manufacturing process require special handling for disposal. The waste streams may comprise a variety of compounds such as diaryl carbonate, aromatic alcohol, aromatic salicylate, polycarbonate oligomers, transesterification catalyst and other high boiling compounds. Currently there is no process to efficiently recover these compounds from a waste stream.

Polycarbonate scrap (i.e., polycarbonate waste from manufacturing processes) can be reacted with alcohols to recover monomers. Aromatic alcohol may be recovered from aromatic salicylate by reacting the aromatic salicylate with an alcohol. The products of both recovery processes need to be further purified to be reused for any other synthesis.

This process is different from recovering compounds from a diaryl carbonate process waste stream. Accordingly, there is a need for waste handling process, which can recover valuable compounds from a diaryl carbonate manufacturing waste stream.

SUMMARY OF INVENTION

Disclosed herein is a method for recovering a product mixture from a diaryl carbonate manufacturing waste stream comprising, reacting the waste stream with an alkyl alcohol to form a reaction mixture, and separating a product mixture from the reaction mixture.

The method as described above can be practiced in an apparatus comprising a reactor, a separation unit, a disposal unit and a plurality of streams transporting reactant and product streams. The reactor is connected to the separation unit by a first transfer stream. The separation unit has a second transfer stream and a product mixture stream. The product mixture stream runs from the separation unit to the diaryl carbonate manufacturing process and the second transfer stream runs from the bottom of the separation unit to the disposal unit.

DETAILED DESCRIPTION

Disclosed herein is a method for recovering valuable compounds from a diaryl carbonate manufacturing waste stream. The method comprises reacting the waste stream with an alkyl alcohol to form a reaction mixture, and separating the product mixture from the reaction mixture. A waste stream is defined as a stream that comprises an amount of diaryl carbonate worth treating to recover a product mixture and at least one waste component that is ultimately disposed of. The waste stream typically comprises at least one catalyst, diaryl carbonate and compounds having boiling points higher than diaryl carbonate. In one embodiment the waste stream comprises transesterification catalyst, diaryl carbonate, optional aromatic salicylate and optional polycarbonate oligomers, and the reaction mixture comprises dialkyl carbonate, aromatic alcohol, alkyl alcohol, a bisphenol, an alkyl salicylate, and unreacted waste. In this embodiment, the product mixture comprises a dialkyl carbonate, an aromatic alcohol and alkyl alcohol.

The method for recovering valuable compounds from diaryl carbonate manufacturing waste streams involves reacting the waste streams with alkyl alcohol. The diaryl carbonate present in the waste streams reacts with alkyl alcohol to produce alkyl aryl carbonate and aromatic alcohol. The alkyl aryl carbonate further reacts with alkyl alcohol to produce dialkyl carbonate and aromatic alcohol. If present, the polycarbonate oligomers in the waste stream react with alkyl alcohol to produce dialkyl carbonate, aromatic alcohol and bisphenol. If present, the aromatic salicylate in the waste streams reacts with alkyl alcohol to produce aromatic alcohol and alkyl salicylate. In the absence of a waste recovery and recycling process valuable compounds such as diaryl carbonate, aromatic salicylate and polycarbonate oligomers present in the waste are lost. The above reactions all have very favorable equilibrium constants.

The reactions occur in presence of the transesterification catalyst although transesterification catalyst may not be required. The reactions are carried out at about atmospheric pressure to a pressure of about 5,000,000 Pascal (Pa) and more preferably about 500,000 to about 2,000,000 Pa, and all subranges therebetween. All pressures described herein are absolute pressures. Higher pressures help to keep the alkyl alcohol in liquid phase. Without being bound by theory, it is presently believed that a catalytic reaction(s) occurs in the liquid phase in presence of transesterification catalyst and non-catalytic reaction(s) may occur in the vapor and liquid phase.

Some of the reaction parameters for the above-mentioned reactions are temperature, reaction time and ratio of alkyl alcohol to the waste being treated. The reaction takes place at a temperature of about 80 to about 250° C. and more preferably at about 140 to about 180° C., and all subranges therebetween. The residence time required for the waste treatment reactions can be up to about 120 minutes. Residence time is defined as the time the waste stays in the reactor at the conditions at which the reactions take place. The waste treatment reactions can be done in a batch or a continuous mode.

The weight ratio of alkyl alcohol to waste stream is maintained at about 0.05 to about 100, preferably about 0.1 to about 40 and most preferably about 0.2 to about 1.5, and all subranges therebetween. Alkyl alcohol availability maximizes the conversion of the waste stream into valuable compounds. Low weight ratios of alkyl alcohol to waste stream results in a lower yield of valuables irrespective of reaction time and temperature. The reactions involved in the waste treatment are exothermic reactions.

When the transesterfication synthesis process is used, the reaction mixture, which is generated when the waste streams react with alkyl alcohol in the waste treatment reaction, comprises alkyl alcohol, aromatic alcohol, dialkyl carbonate, alkyl salicylate, bisphenol, transesterification catalyst, un-reacted waste, and optionally alkyl aryl carbonate. The concentration of alkyl aryl carbonate in the reaction mixture depends residence time, as alkyl aryl carbonate is the intermediate product when diaryl carbonate reacts with alkyl alcohol. With higher residence time all of alkyl aryl carbonate further reacts with alcohol to form dialkyl carbonate and aromatic alcohol. Alkyl aryl carbonate may also be formed when diaryl carbonate reacts with dialkyl carbonate. If a mixture of alkyl alcohol and dialkyl carbonate is reacted with the waste stream, dialkyl carbonate may react with diaryl carbonate present in the waste stream to form alkyl aryl carbonate, which may further react with alkyl alcohol to generate dialkyl carbonate and aromatic alcohol.

Since there is a difference in the boiling point of each of these compounds a product mixture comprising compounds with lower boiling points such as alkyl alcohol, aromatic alcohol and dialkyl carbonate can be separated in a separation unit. Alkyl salicylate present in the reaction mixture can also be recovered along with the product mixture, which may be further purified to recover alkyl salicylate. Bisphenol may further be recovered and recycled back to a polycarbonate polymerization unit or any other synthesis after appropriate purification. After recovery of the product mixture comprising alkyl alcohol, aromatic alcohol and dialkyl carbonate, the remaining mixture comprising bisphenol, transesterification catalyst and un-reacted waste is very viscous. In order to facilitate easy handling of this viscous mixture the separation unit may be designed in such a way that a portion of aromatic alcohol to remains in the mixture comprising bisphenol, transesterification catalyst and un-reacted waste. The presence of aromatic alcohol reduces the viscosity of this mixture, and facilitates handling.

The waste treatment can be achieved by reacting the waste streams either with alkyl alcohol or with a mixture of alkyl alcohol and dialkyl carbonate. The concentration of alkyl alcohol in the mixture may be at about 1% to about 99% by weight. In one embodiment, the mixture of alkyl alcohol and dialkyl carbonate may be an azeotropic mixture formed during the diaryl carbonate manufacturing process.

The alkyl alcohol comprises an aliphatic $C_{1-30}$ monoalcohol, preferably methanol, ethanol and butanol. Suitable aromatic alcohols include, but are not limited to, phenol and alkylphenol such as cresol, xylenol, trimethyl-phenol, tetramethylphenol, ethylphenol, propylphenol, butylphenol, diethylphenol, methylethylphenol, methylpropylphenol, dipropylphenol, methylbutylphenol, pentylphenol, hexylphenol, cyclohexylphenol, and alkoxyphenols such as methoxyphenol and ethyoxyplenol. Suitable dialkyl carbonates, which are useful in the present reaction, include dimethylcarbonate, diethylcarbonate, methylethylcarbonate, ethylpropylcarbonate, dipropylcarbonate, propylbutylcarbonate, dibutylcarbonate, butylpentylcarbonate, dipentylcarbonate, pentylhexylcarbonate, dihexylcarbonate, hexylheptylcarbonate, diheptylcarbonate, heptyloctylcarbonate, dioctylcarbonate, octyinonylcarbonate, dinonylcarbonate, nonyidecylcarbonate, and didecylcarbonate. It is also possible to use combinations of two or more aromatic alcohols and/or dialkyl carbonates.

Preferred classes of transesterification catalysts include titanium compounds like titaniumtetraphenoxide ($Ti(OPh)_4$), and titaniumtetrachloride, organotin compounds, lead compounds, compounds of the copper family metals, zinc complexes, compounds of the iron family metals, and zirconium complexes.

Disclosed herein is a method to recover compounds from waste streams produced in the diaryl carbonate manufacturing process. It will be appreciated by persons skilled in the art that the production of diaryl carbonate can be carried out using various dialkyl carbonates and various aromatic alcohols. The most common reactants used industrially are dimethyl carbonate and phenol, which react to produce diphenyl carbonate. Diaryl carbonate is produced in an energy efficient series of mass and energy integrated reactive distillation columns and distillation columns. This process facilitates high diaryl carbonate production rates, and convenient recovery of unreacted starting materials and side-reaction products for recycle within the process for making diaryl carbonates or utilization in parallel reactions such as the manufacture of dialkyl carbonates.

Figure 1:
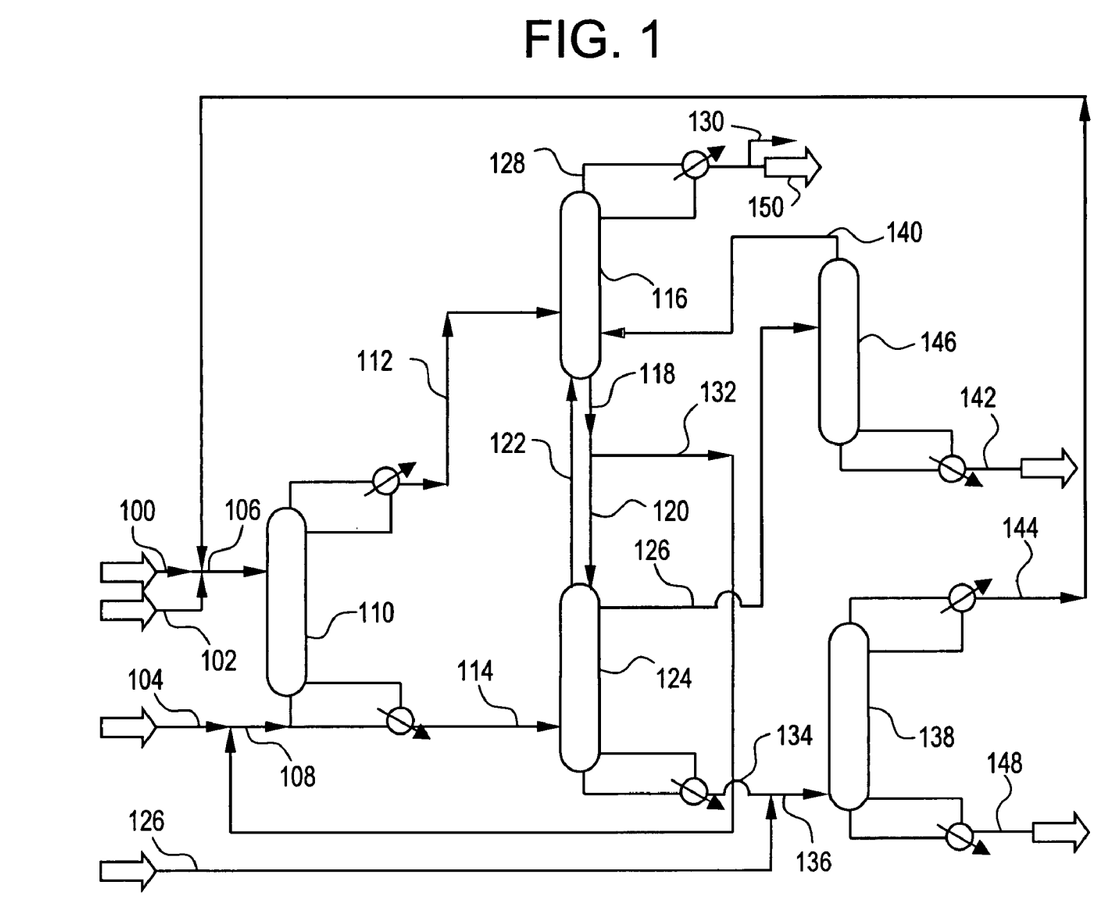
FIG. 1 shows the process of manufacturing diaryl carbonate from a dialkyl carbonate and an aromatic alcohol.

FIG. 1 shows a schematic representation of an exemplary apparatus for manufacturing diaryl carbonate. The apparatus comprises five columns 110, 124, 138, 116 and 146 and various feed, product and recycle streams as indicated by the numbers 100–148.

Columns 110, 124 and 138 are reactive distillation columns. Thus, these columns each have a lower reaction section in which a chemical reaction occurs, and an upper rectification section. The construction of columns of this type is known in the art. In general, the reactive and rectification sections of the column will be furnished with arranged packings, dumped packings or fixed internals. Column 110 provides about 10 to about 80, and more preferably about 15 to about 60 theoretical distillation stages, and all subranges therebetween.

Columns 116 and 146 are rectification columns. These columns are intended to carry out a separation of materials based upon boiling point, without driving a concurrent chemical reaction. The construction of columns of this type is known in the art.

The five columns illustrated in FIG. 1 are interconnected by a series of streams. The direction of flow for each stream is indicated in FIG. 1. Various valves, heaters, and other fittings may be included in adapting the design to a particular installation, and the inclusion of such components is within the skill in the art.

The apparatus depicted in FIG. 1 can be utilized to produce diaryl carbonate. Starting materials are introduced to column 110 through streams 106 and 108. Stream 106 is a combination of stream 100, which comprises mainly aromatic alcohol, either fresh or recycled, and stream 102, which comprises aromatic alcohol and transesterification catalyst. Optionally, stream 106 can also include alkyl alcohol, alkyl carbonate and side-reaction products recycled from reactive distillation column 138 via stream 144. Stream 100 can be further augmented by a fresh transesterification catalyst stream where fresh transesterification catalyst may be added if required.

Stream 108 is a mixture of stream 104, comprising alkyl alcohol and dialkyl carbonate and recycle stream 132 which comprises dialkyl carbonate, aromatic alcohol and side-reaction products recovered from the bottom of rectification column 116.

Stream 108 is fed into the bottom section of column 110, preferably to the reboiler. The stream may be a liquid or a vapor, depending on the type of reboiler used. For example, if an external reboiler, e.g., a kettle reboiler, is used, stream 108 enters column 110 as a vapor. Stream 106 is fed as a liquid into the middle section of column 110, at a location at or near the top of the reactive distillation section. The feed rate of streams 106 and 108 is such that the molar ratio of dialkyl carbonate to aromatic alcohol is about 0.1 to about 10, preferably about 0.5 to about 5 and most preferably about 1 to about 3, and all subranges therebetween. It is particularly advantageous to provide dialkyl carbonate in excess through stream 108, because dialkyl carbonate serves as both a reactant and a stripping agent and facilitates removal of the alkyl alcohol produced in the transesterification reaction. This removal increases the rate of production of alkyl aryl carbonate in column 110. The transesterification reaction in column 110 is carried out at a temperature of about 10020 C. to about 300° C., preferably about 130° C. to about 250° C., and most preferably about 140° C. to about 220° C., and all subranges therebetween. The operating pressure of column 110 is about 5,000 Pascal (Pa) to about 2,000,000 Pa, preferably about 50,000 to about 1,000,000 Pa, and most preferably about 300,000 to about 700,000 Pa, and all subranges therebetween.

Reaction products and unreacted starting materials are removed from column 110 through streams 112 and 114. Stream 112, which is drawn from the head of column 110, comprises unreacted dialkyl carbonate and aromatic alcohol, and alkyl alcohol produced in the transesterification reaction. In one embodiment stream 112 may also contain alkyl aryl ether, a side product of the diaryl carbonate transesterification reaction. This-stream is passed to rectification column 116 for processing and recovery.

Stream 114, which is drawn from near the bottom of column 110, comprises alkyl aryl carbonate, aromatic salicylate and diaryl carbonate produced in column 110, unreacted starting materials and transesterification catalyst. Stream 114 is passed to the second reactive distillation column 124.

Column 124 has a lower reaction section and an upper rectification section. This column promotes the disproportionation of alkyl aryl carbonate into diaryl carbonate and dialkyl carbonate, while at the same time separating dialkyl carbonate from the reaction mixture.

The reactive and rectification sections of column 124 are each furnished with arranged packings, dumped packings or fixed internals to provide about 1 to about 50, preferably about 5 to about 20 theoretical distillation steps, and all subranges therebetween. The temperature in column 124 is about 50 to about 300° C., preferably about 60 to about 280° C., and most preferably about 100 to about 250° C., and all subranges therebetween.

The pressure in column 124 is maintained at about 5,000 Pa to about 1,000,000 Pa, preferably about 20,000 to about 500,000 Pa, and most preferably about 100,000 to about 300,000 Pa, and all subranges therebetween. It is preferable to maintain the pressure of column 124 below the pressure of column 110. This results in an adiabatic flash of stream 114, hence facilitating separation of dialkyl carbonate from the reaction mixture in column 124.

Column 124 is operated in such a way that dialkyl carbonate entering the column through stream 114 is separated from the reaction mixture, hence increasing the rate of the disproportionation reaction taking place in the reactive section. Column 124 can also be utilized as a reboiler for column 116, in which case the two columns are connected by streams 120 and 122 as shown in FIG. 1. In this case, care should be taken to avoid carryover of alkyl aryl carbonate to column 116 in this configuration, since this could result in recycle of alkyl aryl carbonate to column 110 via stream 132. Recycle of alkyl aryl carbonate and alkyl alcohol would drive the composition in column 110 towards the starting materials, hence lowering the net production rate of alkyl aryl carbonate in column 110. Thus, columns 124 and 116 are operated such that stream 120, when present, comprises dialkyl carbonate in the liquid phase, refluxing back from rectification column 116. In one embodiment stream 120 may also comprise alkyl aryl ether and aromatic alcohol.

Stream 122, when present, comprises dialkyl carbonate and the unwanted byproduct alkyl aryl ether (for example anisole) in the vapor phase. This provides energy to drive the separation processes taking place in the column 116. Therefore, heat and mass integration is realized advantageously between columns 124 and 116 via streams 120 and 122.

Rectification column 116 produces a top by-product stream 128 comprising a mixture of dialkyl carbonate and alkyl alcohol produced in the process. In one embodiment the top by-product stream 128 comprises an azeotropic mixture of dialkyl carbonate and alkyl alcohol. In one embodiment stream 128 may be split into stream 130 and stream 150, stream 150 can be condensed and reused as a feed stream for a complementary dialkyl carbonate production process without further purification. Stream 130 can be reused without further purification as a feed stream for recovery of valuable compounds from the waste streams generated from the process of manufacturing diaryl carbonate.

Column 116 is furnished with arranged packings, dumped packings or fixed internals to provide at least about 3 and preferably about 5 to about 50 theoretical distillation steps, and all subranges therebetween. The temperature in the column 116 is about 10 to about 200° C., preferably about 50 to about 150° C., and all subranges therebetween. The pressure in column 116 is at about of 10,000 to about 1,000,000 Pa, preferably about 50,000 to about 200,000 Pa, and all subranges therebetween.

In addition to streams 120 and 122, which interchange materials with column 116, materials leave column 124 via streams 134 and 126. Stream 126, which comprises dialkyl carbonate, alkyl aryl ether and aromatic alcohol, is preferably drawn off as a side stream from column 126 or from bottom of column 116 and fed to a second rectification column 146.

Column 146 separates dialkyl carbonate from alkyl aryl ether, and returns the dialkyl carbonate to column 116 via stream 140. The alkyl aryl ether is discharged through stream 142.

Stream 134 comprises diaryl carbonate produced in column 124, in combination with unreacted starting materials, and some alkyl aryl carbonate, aromatic salicylate, transesterification catalyst and alkyl aryl ether. Stream 134 is fed to reactive distillation column 138, which is furnished with arranged packings, dumped packings or fixed internals. Column 138 provides about 5 to about 80, and more preferably about 20 to about 60 theoretical distillation steps, and all subranges therebetween.

Column 138 is operated to further drive the reaction toward the desired diaryl carbonate product, while separating other materials preferably for recycle. Two streams are removed from column 138. The first is a bottom stream 148, which comprises diaryl carbonate, residual transesterification catalyst, alkyl aryl carbonate and high boiling by-products. Preferably this product stream is further distilled.

The second stream 144 is removed from the top of column 138 comprises unreacted aromatic alcohol, dialkyl carbonate and alkyl aryl ether. Stream 144 is preferably recycled to make up part of stream 106.

Column 138 is operated at a temperature of about 100 to about 300° C., preferably about 100 to about 250° C., and most preferably about 140 to about 200° C., and all subranges therebetween. The pressure in the column is at about 1,000 Pa to about 300,000 Pa, preferably about 5,000 Pa to about 100,000 Pa, and most preferably about 10,000 to about 40,000 Pa, and all subranges therebetween.

Within the scope of the process noted above, several variations are possible. For example, the already described interconnection of columns 116 and 124 via streams 120 and 122.

Additionally stream 134 may be augmented by addition of a stream comprising alkyl aryl carbonate via stream 216 to form stream 136. Preferably stream 216 comprising alkyl aryl carbonate is recovered from the purification of diaryl carbonate.

Figure 2:
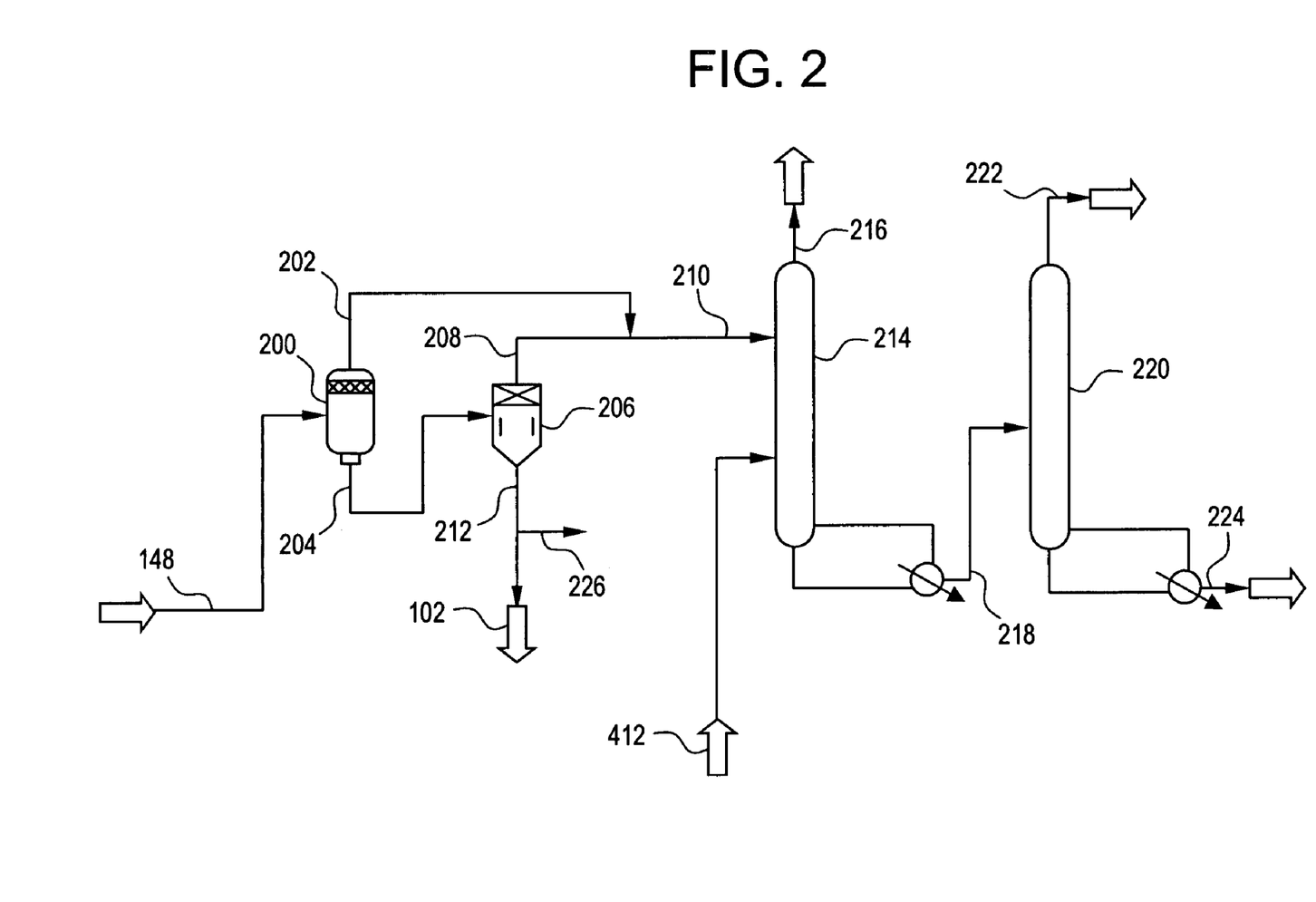
FIG. 2 shows the process for the purification of diaryl carbonate and generation of waste streams.

FIG. 2 shows a schematic representation of an exemplary apparatus for purifying diaryl carbonate, comprising two evaporators 200 and 206, two columns 214 and 220 and various feed, product and recycle streams as indicated by the numbers 200–224.

Evaporators 200 and 206 vaporize the lighter components with lower boiling point. Heat to vaporize the components is supplied by high-pressure steam. The evaporators can be wiped film evaporators, falling film evaporators or a combination of both. Columns 214 and 220 are rectification columns.

The two evaporators and the two columns illustrated in FIG. 2 are interconnected by a series of feed/recycle streams which serve to transport reactants and products. The direction of flow for each such stream is indicated on FIG. 2. Various valves, heaters, and other fittings may be included with these feed/recycle streams in adapting the design to a particular installation, and the inclusion of such components is within the skill in the art.

The apparatus depicted in FIG. 2 can be utilized to purify diaryl carbonate. Stream 148 comprising diaryl carbonate together with residual transesterification catalyst, aromatic alcohol, alkyl aryl carbonate, aromatic salicylate and high boiling by-products is fed to evaporator 200 where diaryl carbonate, alkyl aryl carbonate aromatic alcohol, alkyl alcohol and aromatic alcohol are vaporized and separated from transesterification catalyst and high boiling by-products. Two streams are removed from evaporator 200. The first is a top stream 202 comprising diaryl carbonate, alkyl aryl carbonate, aromatic alcohol, alkyl salicylate and aromatic salicylate. The second stream is a bottom stream 204 comprising diaryl carbonate, transesterification catalyst, aromatic alcohol and high boiling by-products. In one embodiment stream 202 may contain small amount of the transesterification catalyst.

Evaporator 200 is operated at a temperature of about 100 to about 300° C., preferably about 150 to about 250° C., and most preferably about 180 to about 230° C., and all subranges therebetween. The operating pressure in the evaporator is at about 1,000 Pa to about 200,000 Pa and preferably about 1,500 Pa to about 8,000 Pa, and all subranges therebetween.

Stream 204 is fed into evaporator 206 to further recover diaryl carbonate from transesterification catalyst and high boiling by-products. Two streams are recovered from evaporator 206. The first is a top stream 208 comprising diaryl carbonate, alkyl aryl carbonate and transesterification catalyst, which is augmented by mixing with stream 202 to form stream 210. The second stream 212 comprising diaryl carbonate, aromatic salicylate, transesterification catalyst and high boiling by-products is taken from the bottom of evaporator 206. Stream 212 is split into two streams 226 and 102. Stream 102 is recycled to the column 110 and stream 226 is purged as a first waste stream.

Evaporator 206 is operated at a temperature of about 100 to about 300° C., preferably about 150 to about 250° C., and most preferably about 180 to about 230° C., and all subranges therebetween. The operating pressure in the evaporator is at about 1,000 Pa to about 200,000 Pa and preferably about 1,500 Pa to about 8,000 Pa, and all subranges therebetween.

Stream 210 is fed to rectification column 214. This column promotes separation between diaryl carbonate and light components such as aromatic alcohol and alkyl aryl carbonate. Rectification column 214 produces a top stream 216 comprising aromatic alcohol and alkyl aryl carbonate, which may be recycled to augment the feed to reactive distillation column 138. In one embodiment stream 216 may be recycled to reactive distillation column 124. The bottom stream 218 from rectification column 214, comprising diaryl carbonate, polycarbonate oligomers, aromatic salicylate and transesterification catalyst, is fed to rectification column 220 for purification of diaryl carbonate.

Column 214 is furnished with arranged packings, dumped packings or fixed internals to provide at least about 3 and preferably about 5 to about 50 theoretical distillation steps and all subranges therebetween. Column 214 is operated at a temperature of about 100 to about 300° C., preferably about 100 to about 250° C., and most preferably about 140 to about 200° C., and all subranges therebetween. The operating pressure in the column is at about 1,000 Pa to about 300,000 Pa, preferably about 2,000 Pa to about 100,000 Pa, and most preferably about 3,000 to about 8,000 Pa, and all subranges therebetween.

The feed to rectification column 214 can be augmented by recycling the diaryl carbonate recovered from overheads of a polycarbonate polymerizing unit. The recycle stream 412 (shown in FIG. 4) comprising diaryl carbonate and oligomers of polycarbonate may be introduced at the bottom of the rectification column 214.

Stream 218 is fed to the rectification column 220 for further purification of diaryl carbonate. The top stream 222 recovered from column 220 comprises pure diaryl carbonate. The concentration of diaryl carbonate present in stream 222 is about 99.5% relative to weight.

Column 220 is furnished with arranged packings, dumped packings or fixed internals to provide at least about 3 and preferably about 5 to about 50 theoretical distillation steps, and all subranges therebetween. Column 220 is operated at a temperature of about 100 to about 300° C., preferably about 100 to about 250° C., and most preferably about 140 to about 220° C., and all subranges therebetween. The operating pressure in the column is at about 100 Pa to about 300,000 Pa, preferably about 100 Pa to about 100,000 Pa, and most preferably about 100 Pa to about 3,000 Pa, and all subranges therebetween.

The bottom stream 224 from rectification column 220 comprises diaryl carbonate, oligomers of polycarbonate, aromatic salicylate, transesterification catalyst and high boiling by-products. This stream is purged from the diaryl carbonate purification section as a second waste stream.

Figure 3:
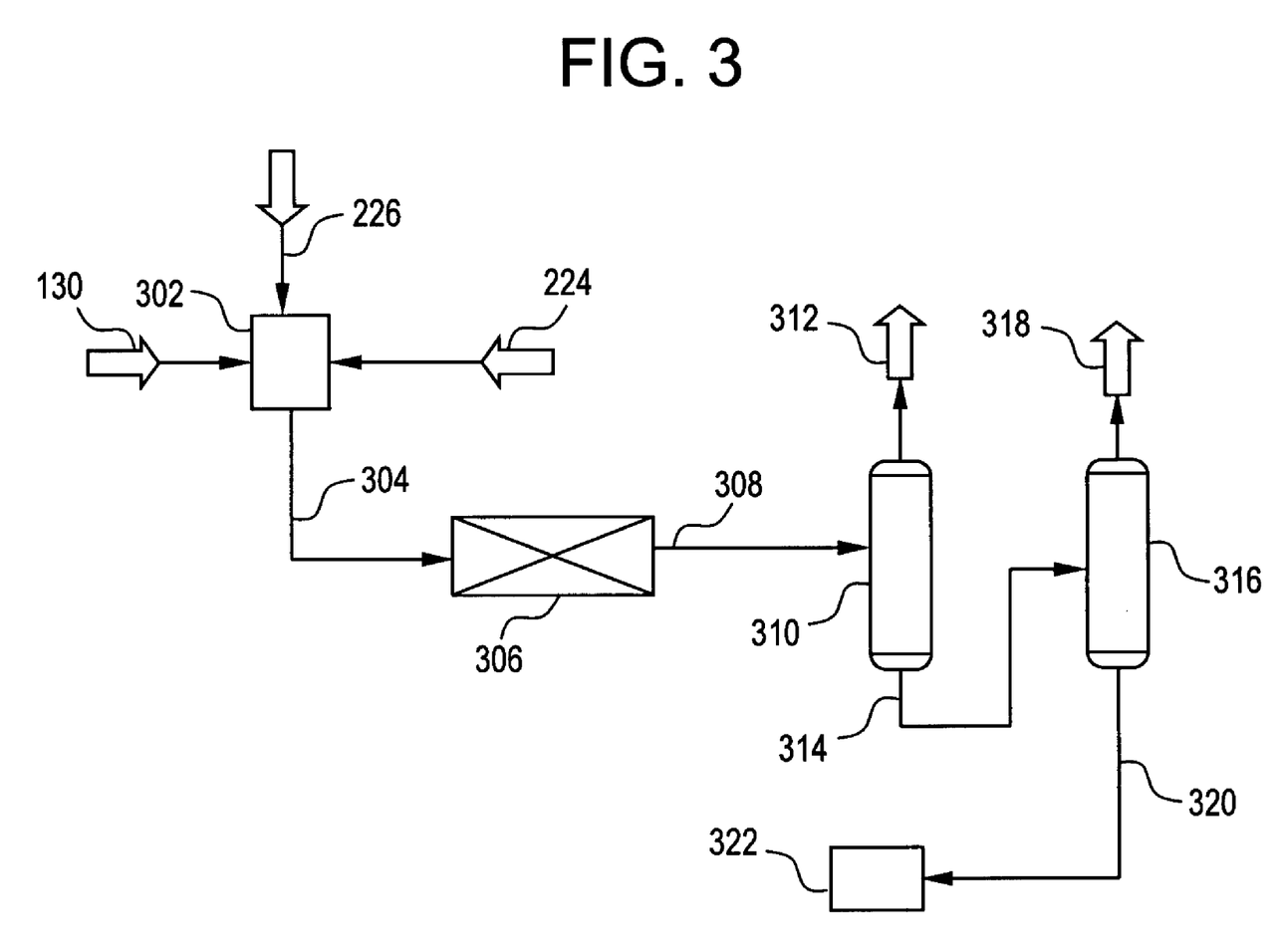
FIG. 3 shows the process for recovery and recycle of compounds from waste streams.

FIG. 3 shows a schematic representation of an exemplary apparatus for recovering compounds from the waste streams. The apparatus comprises a mixing unit 302, a reactor 306, two separation units 310 and 316 and a disposal unit 322. Various feed, product and recycle streams are indicated by the numbers 304–320.

The mixing unit, reactor, two evaporators and disposal unit illustrated in FIG. 3 are interconnected by a series of feed/recycle streams which serve to transport reactants and products. The direction of flow for each such stream is indicated on FIG. 3. Various valves, heaters, and other fittings may be included with these feed/recycle streams in adapting the design to a particular installation, and the inclusion of such components is within the skill in the art.

Waste streams 224 and 226 from the diaryl purification section are introduced into a mixing unit 302 along with stream 130 comprising an azeotropic mixture of dialkyl carbonate and alkyl alcohol. The mixing unit can be an online mixer or any conventional mixing vessel. The mixed stream 304 comprises alkyl alcohol, diaryl carbonate, aromatic salicylate, transesterification catalyst, polycarbonate oligomers and other high boiling by-products. Stream 304 is fed into a reactor 306.

The mixing of the waste streams and stream 130 is required to facilitate the reaction in the reactor. In one embodiment streams 226, 224 and 130 is fed directly into the reactor where it gets mixed. There is no particular limitation in choosing an appropriate reactor for the waste treatment. Various types of conventional reactors such as a plug flow reactor, a continuously stirred tank reactor, a bubble column reactor or a combination of all three or a multi stage stirred tank reactor can be used. In the absence of a mixing unit, if a continuously stirred tank reactor is used, the stirrer in the reactor enhances the mixing and if a plug flow reactor is used the initial length of the reactor is used for mixing. In one embodiment the reactor may be a reactive distillation column.

A combination of more than one reactor or a multistage reactor may be used wherein alkyl alcohol may be added before each reactor for a combination of reactors or in between stages for a multi stage reactor. The reactor is operated with the residence time of the mixed stream 304 in the reactor up to about 120 minutes. The residence time is defined as the time a stream is present in the reactor at reaction conditions.

In the reactor the waste reacts with the alkyl alcohol to generate a reaction mixture comprising aromatic alcohol, bisphenol, alkyl salicylate, unreacted waste feed, unreacted alkyl alcohol, alkyl carbonate and transesterification catalyst. Reactor 306 is operated at a temperature of about 80 to about 250° C. and preferably about 140 to about 180° C., and all subranges therebetween. The reactor pressure is at about atmospheric to about 5,000,000 Pa and preferably about 500,000 Pa to about 2,000,000 Pa, and all subranges therebetween. The ratio of the weight of alkyl alcohol to the combined weight of the waste streams 226 and 224 is maintained at about 0.05 to about 100, preferably at about 0.1 to about 40 and most preferably at about 0.2 to about 1.5, and all subranges therebetween.

The transesterification catalyst concentration in the waste stream is usually sufficient to carry out the reaction of the waste with alkyl alcohol. The concentration of the transesterification catalyst is at least about 0.0001% based on the total weight of the waste feed. Preferably the concentration is about 0.1 to about 10% and most preferably about 1 to about 4%, and all subranges therebetween based on the total weight of the waste feed.

The reaction product stream 308 leaves reactor 306 and is fed into a separation unit 310. This separation unit can be a flash drum, a distillation column, an evaporator, or a combination thereof or any other separation unit known to separate components based on boiling points.

In one embodiment the separation unit 310 is a distillation column. The distillation column is furnished with arranged packings, dumped packings or fixed internals to provide at least about 3 and preferably about 5 to about 50 theoretical distillation steps and all subranges therebetween. This column is operated at a temperature of about 80 to about 250° C. and preferably about 100 to about 225° C. and all subranges therebetween. The operating pressure in the column is at about 100 Pa to about 500,000 Pa, preferably about 100 Pa to about 30,000 Pa and all subranges there between.

In one embodiment the separation unit is a flash drum. The flash drum is operated at a temperature of about 140° C. to about 220° C. and preferably about 150 to about 200° C. and all subranges therebetween. The flash drum operates at a lower pressure than the reactor 306, which enables separation of lighter components by flashing stream 308 into the flash drum. The operating pressure in the flash drum is at about 100 Pa to about 500,000 Pa, preferably about 100 Pa to about 30,000 Pa and all subranges therebetween. In one embodiment the flash drum is attached to a heat exchanger to vaporize the bottom product from the flash drum and recycle part of the vaporized bottom product back into the flash drum. The residence time of the reaction product stream 308 in the flash drum is at about 2 seconds to about 120 minutes, most preferably about five minutes to about sixty minutes. The most efficient time can be determined by one of ordinary skill in the art without undue experimentation by considering parameters such as yield and energy input.

Two streams are recovered from the separation unit 310. The first stream is a product mixture stream 312 comprising alkyl alcohol, aromatic alcohol and alkyl carbonate. Product mixture stream 312 may be recycled back as a feed to the rectification column 214. In one embodiment the product mixture comprises alkyl alcohol, aromatic alcohol, alkyl carbonate and alkyl salicylate and the product mixture may be further purified to separate alkyl salicylate before recycling back to the rectification column 214. The recovered alkyl salicylate may be used for any other synthesis with appropriate purification. The bottom stream 314 from the separation unit 310 comprises bisphenol, transesterification catalyst and un-reacted waste. This stream is sent to a disposal unit. In one embodiment the disposal unit is a burner to incinerate the waste stream.

In one embodiment the bottom stream 314 may be further treated to recover a stream 318 comprising bisphenol wherein stream 314 is fed into a second separation unit 316. Second separation unit 316 can be a distillation column or an evaporator or a combination of both or any other separation unit known to separate components based on differences in vapor pressures. The second separation unit may also be selected based on the differences in solubility in presence of an appropriate solvent. Formation of alkali salts of bisphenol and recovery of the same from stream 314 may also be a process option. Two streams may be recovered from second separation unit 316. The first stream is a second product mixture stream 318 comprising bisphenol. Second product mixture stream 318 may be recycled back in a polycarbonate polymerization unit or used in any other synthesis after appropriate purification. The bottom stream 320 comprising transesterification catalyst and un-reacted waste may be sent to a disposal unit.

Within the scope of the process noted above, several variations are possible. Either or both of the waste streams 226 and 224 and stream 130 can directly be fed to the reactor 306 to recover valuable compounds. Either of the separation units 310 and 316 may be operated to recover product mixture comprising alkyl alcohol, dialkyl carbonate and aromatic alcohol and the second product mixture comprising bisphenol. Stream 314 can directly be sent to the disposal unit if there is no requirement to recover bisphenol. Stream 312 can be sent back to any of the columns 110, 124,138, 214, 116 and 402 (shown in FIG. 4) to integrate the waste treatment unit to the diaryl carbonate production and purification units. Fresh alkyl alcohol in place of stream 130 can be used in suitable quantity as a feed to the reactor 306 to achieve the recovery of the valuable compounds.

Figure 4:
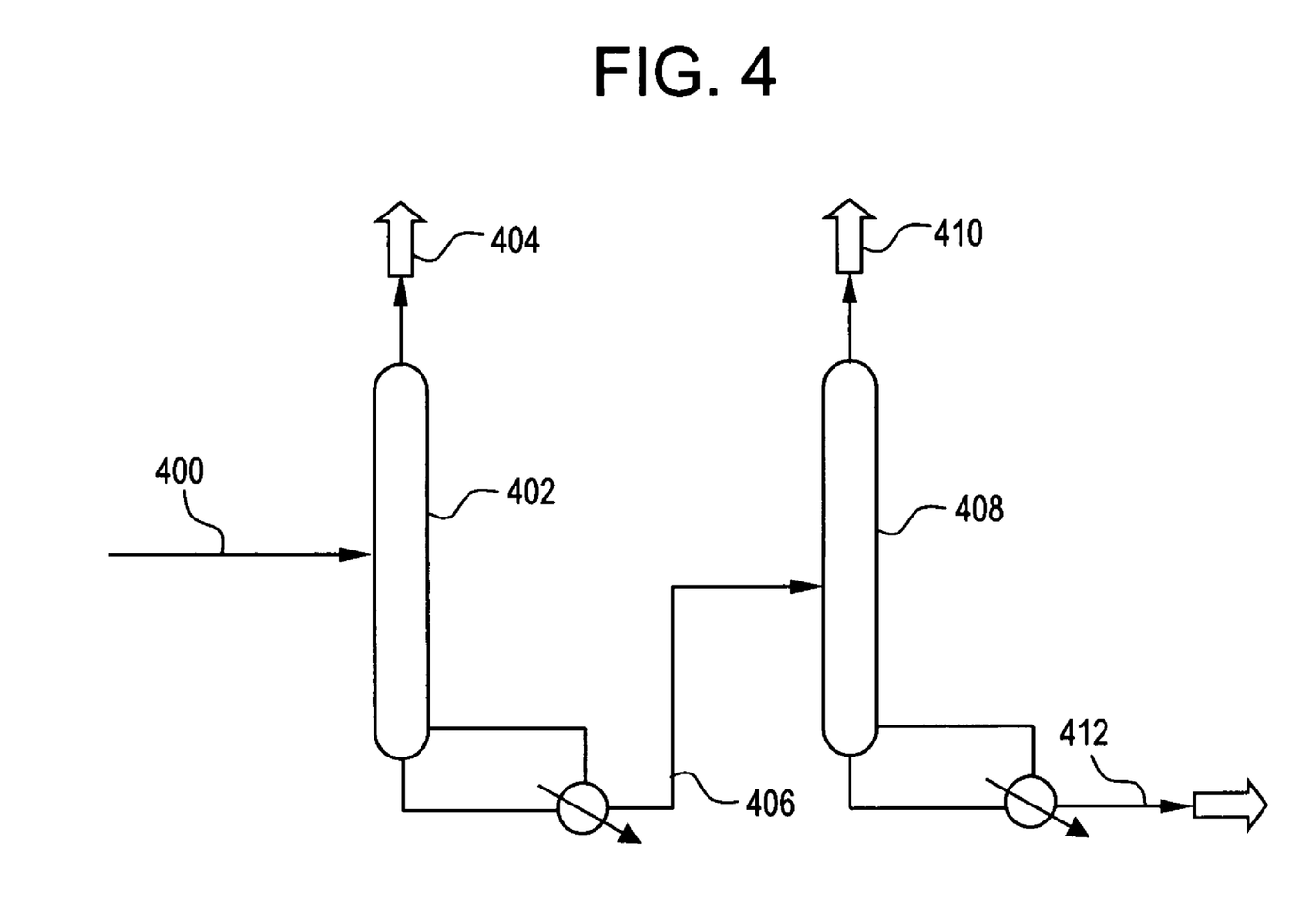
FIG. 4 shows the process for purifying the aromatic alcohol recovered from a polymerization process.

FIG. 4 shows a schematic representation of an exemplary apparatus for purifying and recycling aromatic alcohol from the polycarbonate polymerizer unit comprising two columns 402 and 408. Various feed, product and recycle streams are indicated by the numbers 400–412. Stream 100, as shown in FIG. 1 can be augmented by adding recycled aromatic alcohol recovered from a polycarbonate polymerization process.

Two columns illustrated in FIG. 4 are interconnected by a series of streams. The direction of flow for each stream is indicated on FIG. 4. Various valves, heaters, and other fittings may be included in adapting the design to a particular installation, and the inclusion of such components is within the skill in the art.

During the polycarbonate polymerization, aromatic alcohol is released. Part of the released aromatic alcohol is sent directly to column 110 and part is recycled via stream 400, which is fed into a rectification column 402. Stream 400 comprises aromatic alcohol, diaryl carbonate, bisphenol, and polycarbonate oligomers. The molecular weight (weight averages) of the polycarbonate oligomers is about 300 to about 1500. Rectification column 402 is furnished with arranged packings, dumped packings or fixed internals to provide about 1 to about 50, preferably about 5 to about 20 theoretical distillation steps, and all subranges therebetween. The temperature in the column 402 is about 50 to about 300° C., preferably about 60 to about 280° C., and most preferably about 100 to about 250° C., and all subranges therebetween.

The pressure in column 402 is maintained at about 100 Pa to about 300,000 Pa, preferably about 500 Pa to about 100,000 Pa, and most preferably about 1,000 Pa to about 10,000 Pa, and all subranges therebetween.

Two streams are recovered from column 402. The top stream 404 comprising aromatic alcohol is recycled back to diaryl carbonate process to augment stream 100 as shown in FIG. 1. In one embodiment 404 is drawn from the side of the column 402 to eliminate components lighter than aromatic alcohol. The bottom stream 406 from column 402 comprises aromatic alcohol, diaryl carbonate, bisphenol and polycarbonate oligomers.

Stream 406 is introduced into rectification column 408 to recover aromatic alcohol present in stream 406. The rectification column 408 is furnished with arranged packings, dumped packings or fixed internals to provide about 1 to about 50, preferably about 5 to about 20 theoretical distillation steps, and all subranges therebetween. The temperature in the column 408 is about 50 to about 300° C., preferably about 60 to about 280° C., and most preferably about 100 to about 250° C., and all subranges therebetween.

The pressure in column 408 is maintained at about 100 Pa to about 300,000 Pa, preferably about 500 Pa to about 100,000 Pa, and most preferably about 1,000 Pa to about 10,000 Pa, and all subranges therebetween.

Two streams are recovered from column 408. The top stream 410 comprises aromatic alcohol, which may be recycled back to diaryl carbonate process to augment stream 100 shown in FIG. 1. The bottom stream 412 comprising diaryl carbonate and polycarbonate oligomers may be recycled to diaryl purification process. In one embodiment stream 412 is fed into the bottom of column 214 as shown in FIG. 2, to recover and purify diaryl carbonate present in stream 412.

Polycarbonate oligomers get recycled to diaryl carbonate process by the above-mentioned route through stream 412, as shown in FIG. 4. In one embodiment the recycle streams containing oligomers comprises bisphenol. In another embodiment the recycle streams from polycarbonate polymerizers may be treated with alkyl alcohol directly to recover and recycle dialkyl carbonate and aromatic alcohol. The polycarbonate oligomers are generated in the polycarbonate polymerization process. The polycarbonate is prepared by the transesterification of at least one bisphenol compound, preferably a bisphenol A, with a diaryl carbonate, preferably diphenyl carbonate. The transesterification reaction is performed in the melt and in the presence of one or more transesterification catalysts.

Transesterification catalysts typically comprise at least one alkali metal compound such as an alkali metal hydroxide. An exemplary alkali metal compound is sodium hydroxide (NaOH).

In addition to the transesterification catalyst, a basic co-catalyst may be present. Suitable basic co-catalysts include, but are not limited to, quaternary ammonium compounds, quaternary phosphonium compounds and mixtures thereof. Examples of quaternary ammonium compounds include tetramethylammonium hydroxide (hereinafter sometimes "TMAH"); tetraethylammonium hydroxide; tetra-n-butylammonium hydroxide and trimethylbenzylammonium hydroxide. Examples of quaternary phosphonium compounds include tetramethylphosphonium hydroxide; tetraethylphosphonium hydroxide and tetra-n-butylphosphonium hydroxide. TMAH is usually preferred. The molar ratio of diaryl carbonate to bisphenol compound is generally about 1.01–1.20:1, preferably about 1.05–1.10:1 and all subranges therebetween. The proportion of transesterification catalyst is about 0.01–1,000 and often about 1 molar part per million (ppm) based on the total quantity of bisphenol compound. The proportion of co-catalyst is about 1–10,000 molar ppm, based on the total quantity of bisphenol compound.

Illustrative examples of bisphenol compounds include 1-phenyl 1,1bis (4-hydroxyphenyl)ethane, 1,1-bis(4-hydroxyphenyl), 3,3,5-trimethylcyclohexane, 1,1-bis(3-tert-butyl-4-hydroxy-6-methylphenyl)butane, 2,2-bis(3,5-dimethyl-4-hydroxyphenyl)propane, 1,1-bis(4-hydroxyphenyl)fluorene, 1,1-bis(4-hydroxyphenyl)cyclohexane, 1,1-bis(4-hydroxy-3-methylphenyl)cyclohexane, 1,4-bis[2-(4-hydroxyphenyl)propyl]benzene, 1,3-bis[2-(4-hydroxyphenyl)propyl]benzene, 2,2-bis(3-tert-butyl-4-hydroxyphenyl)propane, 2,2-bis(4-hydroxy-3-methylphenyl)propane, 2,2-bis(4-hydroxy-3-phenylphenyl)propane, 1,1-bis[4-(2-hydroxyethyloxy)phenyl]fluorene, 2,2-bis(4-hydroxyphenyl)propane (Bisphenol A), bis(4-hydroxyphenyl)ether, bis(4-hydroxyphenyl)sulfone, 6,6'-dihydroxy-3,3,3',3'-tetramethyl-1,1'-spirobiindane and the like.

It will be appreciated by persons skilled in the art that the positioning of the various streams as described above as being in the top, middle or bottom of the column is necessarily a relative term since the position at which material is to be introduced is dependent on the conditions being maintained in the column. For example, a stream entering the bottom of the column may actually enter a few stages above the sump, and a stream entering the top of the column may enter a few stages below the top stage. Nonetheless, these terms are included to define the general orientation of the various columns and streams.

The method and apparatus described above allow the recovery and recycle of valuable compounds from waste streams from the process of manufacturing diaryl carbonates in an efficient manner on an industrial scale.

The disclosed method is not limited to the embodiments depicted herein and is capable of recovering compounds from a waste of a diaryl carbonate manufacturing process by any other route. In particular the disclosed process may be applicable for waste from a diaryl carbonate manufacturing process where diaryl carbonate is produced by reacting dialkyl carbonate with aromatic alcohol wherein the dialkyl carbonate is produced by reacting an alkyl alcohol with urea or ethylene glycol carbonate or a cyclic carbonate (e.g., ethylene carbonate). The disclosed method may also be applicable for waste from a diaryl carbonate manufacturing process where diaryl carbonate is produced by reacting phosgene with aromatic alcohol.

The method disclosed here is further illustrated in of the following non-limiting examples.

EXAMPLES 1–8

A batch autoclave of 300 milliliter (ml) volume was used for the reaction of the waste streams wherein the alkyl alcohol chosen for the reaction was methanol at different conditions. The second waste stream comprised 23 weight percent diphenyl carbonate, 1 weight percent phenyl salicylate and 76 weight percent catalyst+oligomers+other compounds. Prior to starting the reactions, the autoclave reactor was tested for any leaks using nitrogen gas at 3,000,000 Pa pressure. Leak test involved pressuring the reactor with nitrogen and then closing the inlets and outlets and monitoring the pressure in the reactor. In example 1 about 100 grams (gms) of second waste stream was loaded into the autoclave along with 21.2 grams (gms) of methanol. The autoclave was heated to a temperature of 180° C. with the stirrer running at a constant RPM of 550. Liquid samples from the reaction mixture were collected at the end of the reaction time and analyzed in a gas chromatograph (GC). Table 1 shows the weight percent of compounds in the reaction mixture after the completion of the reaction. Table 1 also includes dimethyl carbonate, phenol and bisphenol A yields. Yield is calculated as the kilogram of a compound produced per kilogram of waste charged. Results are shown in Table 1.

TABLE 1

|  | Ex. 1 | Ex. 2 | Ex. 3 | Ex.4 | Ex.5 | Ex.6 | Ex.7 | Ex.8 |
| --- | --- | --- | --- | --- | --- | --- | --- | --- |
| Temperature (° C.) | 180 | 220 | 180 | 220 | 180 | 220 | 180 | 220 |
| Residence Time (minute) | 30 | 30 | 60 | 60 | 30 | 30 | 60 | 60 |
| Methanol/waste (gram/gram) | 21.2/100 | 21.1/100 | 21.1/100 | 21.22/100 | 42.4/100 | 42.4/100 | 42.4/100 | 42.2/100 |
| Pressure (Pascal) | 482759 | 655172 | 448276 | 586207 | 827586 | 1379310 | 931034 | 1379310 |
| Compound Name | Analysis of reaction mixture after reaction completion | | | | | | | |
| Methanol | 0 | 0 | 0 | 0 | 8.4 | 7.96 | 8.46 | 10.07 |
| Dimethyl carbonate | 17 | 17 | 17.8 | 15.92 | 24.2 | 23.7 | 23.51 | 24.7 |
| Phenol | 20 | 22.97 | 22.52 | 21.19 | 23.84 | 23.73 | 22.36 | 23.25 |
| Phenyl methyl carbonate | 9.1 | 9.1 | 8.18 | 8.3 | 0.03 | 0.07 | 0.1 | 0.067 |
| Methyl salicylate | 1.02 | 1.02 | 1.02 | 1 | 1.1 | 1.08 | 1.03 | 1.05 |
| Diphenyl carbonate | 0.8 | 0.72 | 0.83 | 0.62 |  | 0.05 | 0.05 | 0.08 |
| Phenyl salicylate | 0.1 | 0.2 | 0.15 | 0.13 |  | 0 | 0 | 0.02 |
| Bisphenol A | 20.5 | 20.52 | 20.38 | 18.87 | 31.1 | 26.71 | 27.27 | 31.4 |
| sum | 68.52 | 71.53 | 70.88 | 65.99 | 88.67 | 83.34 | 82.84 | 90.64 |
| Catalyst + oligomers + others | 31.48 | 28.47 | 29.12 | 34.01 | 11.33 | 16.66 | 17.16 | 9.37 |
| Compound Name | Yields based on waste (kilogram/kilogram of waste) | | | | | | | |
| Dimethyl carbonate | 20.57 | 20.57 | 21.54 | 19.26 | 34.36 | 33.65 | 33.38 | 35.07 |
| Phenol | 24.2 | 27.78 | 27.3 | 25.6 | 33.9 | 33.7 | 31.8 | 33 |
| Bisphenol A | 24.8 | 24.8 | 24.7 | 22.8 | 44.2 | 37.9 | 38.7 | 44.6 |

EXAMPLES 9–10

Using the same apparatus described in example 1, experiments 9–10 were carried out under the reaction conditions indicated in Table 2. In examples 9–10 the waste taken for reaction was a mixture of first and second waste stream from a diphenyl carbonate manufacturing process. The composition of the mixture of the first and second waste stream and the reaction results are given in Table 2.

TABLE 2

|  | mixture of first and second waste stream | Ex. 9 | Ex. 10 |
| --- | --- | --- | --- |
| Mixed waste grams |  | 180.6 | 177.9 |
| Methanol grams |  | 37.9 | 37.9 |
| Total feed grams |  | 218.5 | 215.8 |
| T ° C. |  | 218.5 | 215.8 |
| P Pascal |  | 680272.1 | 680272.1 |

TABLE 2-continued

| Component ID | mixture of first and second waste stream | Ex. 9 | Ex. 10 |
|---|---|---|---|
| | Weight % | | |
| Dimethyl carbonate | | 18.0 | 21.0 |
| Phenol | 4.9 | 33.9 | 32.7 |
| Bisphenol A | | 24.4 | 23.5 |
| Methyl Salicylate | | 2.4 | 2.4 |
| Diphenyl Carbonate | 21.5 | 0.0 | 0.0 |
| Phenyl salicylate | 4.2 | 0.0 | 0.0 |
| Catalyst + Oligomer + Others | 69.5 | 21.3 | 20.4 |
| Total | 100.0 | 100.0 | 100.0 |
| Component ID | Yield (kilogram/kilogram of waste) | | |
| Dimethyl carbonate | | 21.8 | 25.5 |
| Phenol | | 41.0 | 39.6 |
| Bisphenol A | | 29.5 | 28.5 |

EXAMPLES 11–29

A plug flow reactor was used to react methanol with the second waste stream in a continuous mode. Total volume of the reactor was 105.1 ml. The length and diameter of the reactor were 50 and 1.62 centimeters (cm). Methanol and second waste stream were mixed in a mixer. The methanol to waste stream weight ratio (MeOH/WS) is shown in Table 3. The mixture of methanol and second waste stream was pumped into the plug flow reactor using a gear pump. The residence time (RT) is shown in Table 3. The reactor was heated to a temperature as shown in Table 3 in degrees Celsius and the pressure in the reactor was 3,027,211 Pascal. Samples were taken from the exit of the reactor and analyzed using a GC. The results are given in Table 3. The reaction was continued for 60 minutes.

TABLE 3

| | Ex. 11 | Ex. 12 | Ex. 13 | Ex. 14 | Ex. 15 | Ex. 16 | Ex. 17 | Ex. 18 | Ex. 19 | Ex. 20 | Ex. 21 | Ex. 22 | Ex. 23 | Ex. 24 | Ex. 25 | Ex. 26 | Ex. 27 | Ex. 28 | Ex. 29 |
|---|---|---|---|---|---|---|---|---|---|---|---|---|---|---|---|---|---|---|---|
| Temp. | 161 | 180 | 151 | 140 | 181 | 161 | 141 | 141 | 160 | 180 | 141 | 161 | 181 | 150 | 170 | 160 | 160 | 160 | 160 |
| RT | 17.65 | 17.86 | 17.80 | 17.44 | 17.47 | 17.77 | 19.26 | 19.48 | 19.79 | 18.99 | 6.36 | 6.13 | 6.47 | 6.39 | 6.28 | 13.30 | 12.64 | 17.64 | 17.28 |
| MeOH/WS | 0.37 | 0.36 | 0.35 | 0.37 | 0.23 | 0.22 | 0.22 | 0.51 | 0.53 | 0.47 | 0.36 | 0.37 | 0.38 | 0.38 | 0.36 | 0.41 | 0.37 | 0.43 | 0.40 |
| Name of compound | | | | | | | | | | | | | | | | | | | |
| | Analysis of reaction mixture after reaction completion (weight %) | | | | | | | | | | | | | | | | | | |
| Methanol | 8.86 | 7.31 | 7.38 | 9.52 | 0.38 | 0.64 | 1.26 | 18.11 | 17.14 | 16.15 | 13.64 | 10.48 | 9.22 | 13.33 | 10.02 | 11.83 | 8.33 | 13.23 | 10.70 |
| Dimethyl carbonate | 27.37 | 28.51 | 25.91 | 24.30 | 25.13 | 24.88 | 20.95 | 22.58 | 24.99 | 24.03 | 14.25 | 20.14 | 25.16 | 17.43 | 23.02 | 23.10 | 24.56 | 25.52 | 25.02 |
| Anisole | 0.05 | 0.04 | 0.05 | 0.06 | 0.02 | 0.03 | 0.04 | 0.01 | 0.01 | 0.01 | 0.03 | 0.03 | 0.03 | 0.01 | 0.02 | 0.03 | 0.03 | 0.02 | 0.03 |
| Phenol | 27.82 | 27.84 | 27.44 | 27.00 | 31.61 | 31.22 | 27.82 | 24.58 | 25.33 | 27.46 | 23.22 | 27.80 | 30.08 | 26.29 | 28.82 | 29.04 | 29.48 | 29.39 | 30.61 |
| Phenyl methyl carbonate | 0.34 | 0.14 | 1.89 | 2.59 | 3.25 | 3.51 | 6.42 | 1.69 | 0.20 | 0.03 | 7.00 | 3.97 | 1.05 | 4.97 | 1.62 | 0.90 | 0.78 | 0.29 | 0.36 |
| Methyl Salicylate | 0.96 | 0.93 | 0.91 | 0.91 | 1.63 | 1.64 | 0.96 | 0.83 | 0.86 | 1.43 | 1.28 | 1.32 | 1.33 | 1.32 | 0.67 | 1.30 | 1.34 | 1.33 | 1.40 |
| Diphenyl carbonate | 0.00 | 0.00 | 0.05 | 0.11 | 0.10 | 0.01 | 0.59 | 0.15 | 0.00 | 0.00 | 3.53 | 0.94 | 0.04 | 1.29 | 0.05 | 0.02 | 0.01 | 0.00 | 0.00 |
| Phenyl salicylate | 0.00 | 0.00 | 0.00 | 0.00 | 0.05 | 0.04 | 0.01 | 0.00 | 0.00 | 0.00 | 0.02 | 0.00 | 0.00 | 0.01 | 0.00 | 0.00 | 0.00 | 0.00 | 0.00 |
| Bisphenol | 29.52 | 30.69 | 27.75 | 25.92 | 26.17 | 25.13 | 21.84 | 24.65 | 27.19 | 25.71 | 13.69 | 20.96 | 26.21 | 18.03 | 25.64 | 25.73 | 27.00 | 24.86 | 26.07 |
| Catalyst + oligomers + others | 507 | 4.53 | 8.62 | 9.59 | 11.65 | 12.91 | 20.11 | 7.41 | 4.29 | 5.18 | 23.34 | 14.36 | 6.88 | 17.33 | 10.13 | 8.05 | 8.47 | 5.37 | 5.82 |
| Name of compound | | | | | | | | | | | | | | | | | | | |
| | Yields | | | | | | | | | | | | | | | | | | |
| Dimthyl carbonate | 37.55 | 38.77 | 34.98 | 33.29 | 30.91 | 30.35 | 25.49 | 34.10 | 38.23 | 35.30 | 19.43 | 27.59 | 34.72 | 24.05 | 31.31 | 32.58 | 33.65 | 34.96 | 34.28 |
| Phenol | 38.17 | 37.56 | 37.04 | 36.99 | 38.88 | 38.09 | 33.86 | 37.11 | 38.76 | 40.34 | 31.67 | 38.09 | 41.51 | 36.28 | 39.20 | 40.95 | 40.38 | 40.26 | 41.94 |
| Bisphenol A | 40.51 | 41.74 | 37.47 | 35.51 | 32.19 | 30.66 | 26.58 | 37.22 | 41.60 | 37.77 | 18.66 | 28.71 | 36.16 | 24.89 | 34.87 | 36.28 | 36.98 | 34.06 | 35.71 |

As can be seen from the foregoing examples, the waste stream for a process to produce diaryl carbonate can be reacted with an alkyl alcohol and valuable compounds can be recovered.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for recovering a product mixture from a diaryl carbonate manufacturing waste stream comprising;
   reacting said waste stream with an alkyl alcohol to form a reaction mixture comprising said product mixture and at least one waste component; and
   separating said product mixture from said reaction mixture.

2. The method according to claim 1 wherein said reaction occurs in liquid phase or a combination of liquid and vapor phase.

3. The method according to claim 1 wherein said reaction occurs in a batch or a continuous mode.

4. The method according to claim 1 wherein said reaction occurs at a temperature of about 80to about 250° C.

5. The method according to claim 1 wherein said reaction occurs at a temperature of about 140to about 180° C.

6. The method according to claim 1 wherein maid reaction is carried out at a pressure of about atmospheric pressure to about 5,000,000 Pascal.

7. The method according to claim 1 wherein said reaction is carried out at a pressure of about 500,000 to about 2,000,000 Pascal.

8. The method according to claim 1 wherein the weight ratio of said alkyl alcohol to said waste stream is maintained at about 0.05 to about 100.

9. The method according to claim 1 wherein the weight ratio of said alkyl alcohol to said waste stream is maintained at about 0.2 to about 1.5.

10. The method according to claim 1 wherein said waste stream comprises transesterification catalyst, diaryl carbonate, aromatic salicylate and polycarbonate oligomers and said product mixture comprises a dialkyl carbonate, aromatic alcohol, alkyl salicylate and said alkyl alcohol.

11. The method according to claim 10 wherein the concentration of said transesterification catalyst is at about 0.0001% to about 10% by weight relative to said waste stream.

12. The method according to claim 10 wherein the concentration of said transesterification catalyst is at about 0.1% to about 10% by weight relative to said waste stream.

13. The method according to claim 10 wherein the concentration of said transesterification catalyst is at about 1% to about 4% by weight relative to said waste.

14. The method according to claim 1 wherein after separation of said product mixture, the waste component is disposed of.

15. The method according to claim 1 wherein said waste stream further comprises a first waste stream and a second waste stream.

16. The method according to claim 15 wherein said first waste stream comprises said transesterification catalyst, said diaryl carbonate and said aromatic salicylate and said second waste stream comprises said diaryl carbonate, polycarbonate oligomers, aromatic salicylate and transesterification catalyst.

17. The method according to claim 1 wherein said waste stream and said alkyl alcohol is mixed before reacting.

18. The method according to claim 17 wherein said waste stream and said alkyl alcohol is mixed in an online mixer or a mixing vessel.

19. The method according to claim 1 wherein a mixture of said alkyl alcohol and said dialkyl carbonate is used to react with said waste stream and the concentration of said alkyl alcohol in said mixture is about 1% to about 99% by weight.

20. A method for recovering a product mixture from a waste stream in a diaryl carbonate manufacturing process comprising:
   introducing reactant streams comprising a dialkyl carbonate, an aromatic alcohol and a transesterification catalyst to a first reactive distillation column;
   recovering from said first reactive distillation column a first top stream comprising said dialkyl carbonate, an alkyl alcohol, an alkyl aryl ether and said aromatic alcohol and a first bottom stream comprising an alkyl aryl carbonate, said transesterification catalyst, diaryl carbonate and an aromatic salicylate;
   introducing said first bottom stream into a second reactive distillation column to produce a diaryl carbonate;
   recovering from said second reactive distillation column a first side stream comprising said dialkyl carbonate, aromatic alcohol, alkyl aryl ether and a second bottom stream comprising said diaryl carbonate, alkyl aryl carbonate, transesterification catalyst, aromatic salicylate and dialkyl carbonate;
   introducing said first side stream into a second rectification column to separate a dialkyl carbonate stream from said alkyl aryl ether and said aromatic alcohol, and recycling said dialkyl carbonate stream to a first rectification column;
   introducing said second bottom stream to a third reactive distillation column;
   recovering from said third reactive distillation column a second top stream comprising unreacted said aromatic alcohol, dialkyl carbonate and alkyl aryl ether and recycling said second top stream to said first reactive distillation column;
   introducing said first top stream into said first rectification column;
   recovering from said first rectification column a first azeotrope top stream comprising said dialkyl carbonate/alkyl alcohol azeotrope, and a third bottom stream comprising said dialkyl carbonate, aromatic alcohol and alkyl aryl ether and recycling said third bottom stream to said first reactive distillation column;
   recovering a fourth bottom stream comprising said diaryl carbonate from the bottom of said third reactive distillation column and introducing said fourth bottom stream into a first evaporator;
   recovering ftom said first evaporator a third top stream comprising said diaryl carbonate, alkyl aryl carbonate, aromatic alcohol, an alkyl salicylate and an aromatic salicylate and a fifth bottom stream comprising said diaryl carbonate, aromatic salicylate and transesterification catalyst and introducing said fifth bottom stream into a second evaporator;

recovering from said second evaporator a fourth top stream comprising said diaryl carbonate and a sixth bottom stream comprising said transesterification catalyst, said diaryl carbonate and said aromatic salicylate;

splitting said sixth bottom stream into a first recycle stream and a first bottom waste stream and recycling said first recycle stream into said first reactive distillation column;

introducing said third top stream and said fourth top stream into a third rectification column;

recovering from said third rectification column a fifth top stream comprising said alkyl aryl carbonate and aromatic alcohol and a seventh bottom stream comprising said diaryl carbonate, polycarbonate oligomers, said aromatic salicylate and said transesterification catalyst;

introducing said fifth top stream to said third reactive distillation column and introducing said seventh bottom stream into a fourth rectification column;

recovering from said fourth rectification column a sixth top stream comprising said diaryl carbonate and a second bottom waste stream comprising said diaryl carbonate, polycarbonate oligomers, aromatic salicylate arid transesterification catalyst;

introducing said second bottom waste stream, said first bottom waste stream and said alkyl alcohol into a mixing unit to produce said waste stream;

introducing said waste stream into one or more reactors;

reacting said waste stream with said alkyl alcohol to form a reaction mixture;

introducing said reaction mixture into a separating unit;

recovering from said separation unit a product mixture and an eighth bottom stream comprising a bisphenol, said transesterification catalyst and unreacted waste;

recycling said product mixture into said third rectification column; and introducing said eighth bottom stream into a disposal unit, wherein said product mixture comprises a dialkyl carbonate, an aromatic alcohol and said alkyl alcohol; said waste stream comprises a transesterification catalyst, said diaryl carbonate, an aromatic salicylate and polycarbonate oligomers; and said reaction mixture comprises said dialkyl carbonate, said aromatic alcohol, said alkyl alcohol, a bisphenol, an alkyl salicylate, and unreacted waste.

21. The method according to claim 20 wherein said alkyl alcohol is introduced directly to said reactor.

22. The method according to claim 20 wherein part of said first azeotrope top stream is used to react with said waste stream.

23. The method according to claim 22 wherein part of said first azeotrope stream is introduced to said mixing unit.

24. The method according to claim 22 wherein part of said azeotrope stream is sent directly to said reactor.

25. The method according to claim 20 wherein said first bottom waste stream and said second waste stream are introduced directly into said reactor.

26. The method according to claim 20 wherein said reactor is selected from the group consisting continously stirred tank reactor, plug flow reactor and bubble column reactor.

27. The method according to claim 20 wherein said reactor is a combination of a continuously stirred tank reactor, a plug flow reactor and a bubble column reactor.

28. The method according to claim 20 wherein residence time in said reactor is up to about 120 minutes.

29. The method according to claim 20 wherein said separation unit is selected from the group consisting flash drum, distillation column and evaporator.

30. The method according to claun 29 wherein said separation unit is a distillation column.

31. The method according to claim 30 wherein said distillation column is maintained at a temperature of about 100 to about 220° C.

32. The method according to claim 30 wherein said distillation column is maintained at a pressure of about 100 Pascal to about 500,000 Pascal.

33. The method according to claim 30 wherein said distillation column is maintained at a pressure of about 100 to about 30,000 Pascal.

34. The method according to claim 29 wherein said separation unit is a flash drum.

35. The method according to claim 34 wherein said flash drum is maintained at a temperature of about 140 to about 220° C.

36. The method according to claim 34 wherein said flash drum is maintained at a pressure of about 100 Pascal to about 500,000 Pascal.

37. The method according to claim 34 wherein said flash drum is maintained at a pressure of about 100 to about 30,000 Pascal.

38. The method according to claim 20 wherein said product mixture is recycled back to a column selected from the group of columns consisting said first, second and third reactive distillation column and first and third rectification column.

39. The method according to claim 20 wherein said eighth bottom stream is further purified to recover said bisphenol.

40. The method according to claim 39 wherein said recovered bisphenol is recycled to polycarbonate polymerization process.

41. The method according to claim 20 wherein said disposal unit is a burner.

42. The method according to claim 20 wherein maid product mixture further comprises an alkyl salicylate.

43. The method according to claim 42 wherein said product mixture is further purified to recover said alkyl salicylate.

* * * * *